US007988913B2

(12) United States Patent
Numajiri

(10) Patent No.: US 7,988,913 B2
(45) Date of Patent: Aug. 2, 2011

(54) BIOCHEMICAL REACTION CARTRIDGE

(75) Inventor: Yasuyuki Numajiri, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 11/549,204

(22) Filed: Oct. 13, 2006

(65) Prior Publication Data

US 2007/0071637 A1 Mar. 29, 2007

Related U.S. Application Data

(62) Division of application No. 10/811,917, filed on Mar. 30, 2004, now abandoned.

(30) Foreign Application Priority Data

Mar. 31, 2003 (JP) ................................ 2003-094241
Mar. 31, 2003 (JP) ................................ 2003-097136

(51) Int. Cl.
*G01N 21/00* (2006.01)
*G01N 21/75* (2006.01)
*C12M 1/34* (2006.01)

(52) U.S. Cl. ........................ 422/65; 422/401; 435/288.4

(58) Field of Classification Search .................... 422/57, 422/58, 65, 401; 435/288.4
See application file for complete search history.

(56) References Cited

U.S. PATENT DOCUMENTS 4,690,899 A * 9/1987 Klose et al. .................... 436/45
5,370,842 A 12/1994 Miyazaki et al. .......... 422/82.06
5,445,934 A 8/1995 Fodor et al. ....................... 435/6
5,587,128 A * 12/1996 Wilding et al. ................. 422/50
5,637,469 A 6/1997 Wilding et al. .............. 435/7.21
5,690,763 A 11/1997 Ashmead et al. ............... 156/60
5,863,502 A 1/1999 Southgate et al. .............. 422/58
5,928,880 A 7/1999 Wilding et al. .............. 435/7.21
6,043,080 A 3/2000 Lipshutz et al. ........... 435/287.2
6,150,180 A 11/2000 Parce et al. ................... 436/514
6,167,910 B1 1/2001 Chow ............................ 137/827
6,184,029 B1 2/2001 Wilding et al. ............ 435/287.1
6,274,337 B1 8/2001 Parce et al. ..................... 435/29
6,399,389 B1 6/2002 Parce et al. ...................... 436/47
6,494,230 B2 12/2002 Chow ............................ 137/827
6,503,757 B1 1/2003 Chow .............................. 436/43
6,551,841 B1 4/2003 Wilding et al. ............... 436/518
6,805,841 B2 10/2004 Shvets et al. .................. 422/100
2002/0063060 A1 5/2002 Gascoyne et al. ............ 204/471
2002/0192112 A1 12/2002 Chow .............................. 422/63
2004/0224339 A1 11/2004 Numajiri et al. .................. 435/6

FOREIGN PATENT DOCUMENTS

JP 2832117 B2 9/1998
JP 11-509094 8/1999
JP 2000-274375 10/2000

OTHER PUBLICATIONS

Angelika Lueking et al., "Protein Microarrays for Gene Expression and Antibody Screening," 270 *Anal. Biochem.* 103-11 (1999).

* cited by examiner

*Primary Examiner* — Lore Jarrett
(74) *Attorney, Agent, or Firm* — Fitzpatrick, Cella, Harper, Scinto

(57) ABSTRACT

A biochemical reaction cartridge includes an injection port for injecting a specimen, a chamber for containing the specimen therein, a chamber for containing a reagent for treating the specimen, nozzle ports for applying or reducing pressure by using fluid. In the cartridge, the specimen is subjected to a biochemical reaction by controlling the fluid. The cartridge is mounted in a biochemical reaction apparatus.

7 Claims, 5 Drawing Sheets

BIOCHEMICAL REACTION CARTRIDGE

This application is a division of application Ser. No. 10/811,917, filed Mar. 30, 2004, which is incorporated herein by reference.

FIELD OF THE INVENTION AND RELATED ART

The present invention relates to a technology to analyze a cell, a microorganism, a chromosome, a nucleic acid, etc., in a specimen by utilizing a biochemical reaction. More specifically, the present invention relates to a biochemical reaction cartridge for use in the analysis and a biochemical treatment apparatus for effecting the biochemical reaction in the cartridge.

Most analyzers for analyzing specimens, such as blood, use an immunological procedure utilizing an antigen-antibody reaction or a procedure utilizing nucleic acid hybridization. For example, a protein, such as an antibody or antigen, or a single-stranded nucleic acid, which specifically connects with a material or substance to be detected, is used as a probe and is fixed on a surface of a solid phase, such as fine particles, beads or a glass plate, thus effecting an antigen-antibody reaction or nucleic acid hybridization. Then, for example, an antigen-antibody compound or a double-stranded nucleic acid is detected by a labeled antigen or labeled nucleic acid, which causes a specific interaction, such that a labeled material having a high detection sensitivity, such as an enzyme, a fluorescent material or a luminescent material, is supported, thus effecting detection of the presence or absence of the material to be detected or a quantitative determination of the detected material.

As an extension of these technologies, e.g., U.S. Pat. No. 5,445,934 discloses a so-called DNA (deoxyribonucleic acid) array, wherein a large number of DNA probes having mutually different base sequences are arranged on a substrate in an array form.

Further, Anal. Biochem., 270(1), pp. 103-111 (1999), discloses a process for preparing a protein array, like a DNA array, such that various species of proteins are arranged on a membrane filter. By using these DNA and protein arrays and the like, it has become possible to effect a test on a large number of items at the same time.

Further, in various methods of specimen analysis, in order to avoid contamination of the specimen, promote reaction efficiency, reduce the size of the apparatus, and facilitate the operation, there have been also proposed disposable biochemical reaction cartridges in which a necessary reaction is performed. For example, Japanese Laid-Open Patent Application (JP-A) (Tokuhyo) Hei 11-509094 disclose a biochemical reaction cartridge, including a DNA array, in which a plurality of chambers are disposed, and a solution is moved by a differential pressure so as to permit a reaction, such as extraction, amplification or hybridization of DNA in a specimen, within the cartridge. U.S. Pat. No. 5,690,763 discloses a structure that can be used for conducting a reaction that has a three-dimensionally curved passage through laminated sheets. U.S. Pat. Nos. 6,167,910 and 6,494,230 discloses structures of μ-TAS (micro-total analysis system), wherein a passage is provided between a first layer and a second layer and between a second layer and a third layer, constituting a three-layer structure, and the respective passages are partially connected with each other.

In order to externally inject a solution into such biochemical reaction cartridges, it is possible to utilize an external syringe or a vacuum pump. Also, the solution within the biochemical reaction cartridges may be moved by gravity, capillary action, and electrophoresis. Further, a compact micropump can be provided inside of the biochemical reaction cartridge. Japanese Patent No. 2832117 discloses a pump utilizing a heat-generating element. JP-A (Tokkai) 2000-274375 discloses a pump utilizing a piezoelectric element. JP-A (Tokuhyo) Hei 11-509094 discloses a diaphragm pump.

As described above, it is preferable to use a disposable cartridge containing a necessary solution from the viewpoint of prevention of a secondary infection or contamination and usability. However, a cartridge containing a pump is expensive.

Further, in the conventional biochemical reaction cartridges, such as μ-TAS, there is no disclosure as to how to properly move the liquid only by injecting, for example, a reagent or a liquid specimen in one direction and achieving a reciprocating motion. Particularly, there is a problem in that when the entire amount of the liquid is moved by conventional methods, bubbles are generated when the movement is completed. Thus, the entire amount of the liquid cannot be moved completely without generating bubbles.

SUMMARY OF THE INVENTION

An object of the present invention is to provide a disposable biochemical reaction cartridge structured so that a biochemical reaction can proceed by moving a solution using an external pumping action without the cartridge itself containing a pump and being capable of preventing the solution from flowing out of the cartridge.

Another object of the present invention is to provide a biochemical treatment apparatus for effecting the biochemical reaction within the cartridge by using the biochemical reaction cartridge described above.

Another object of the present invention is to provide a method of using a biochemical reaction cartridge capable of ensuring an appropriate movement in such a manner that an optimum passage is selected and used properly with respect to the movement of a reagent or a specimen only requiring injection into a subsequent chamber and movement of a reaction liquid requiring a reciprocating motion.

According to the present invention, there is provided a biochemical reaction cartridge, comprising:

an injection port for injecting a specimen therefrom, a first chamber for containing the specimen therein, a second chamber for containing therein a reagent, which contributes to a biochemical reaction, a passage for passing therethrough the specimen and/or the reagent and/or a reaction liquid, and a plurality of nozzle ports for receiving therethrough a plurality of nozzles for applying or reducing pressure, wherein the plurality of nozzle ports communicate with the first or second chamber, and fluid is present between the plurality of nozzle ports and the first or second chamber and is pressurized or depressurized by the plurality of nozzles to move the specimen and/or the reagent and/or the reaction liquid, thereby effecting a sequence of a biochemical reaction within the cartridge.

According to the present invention, there is also provided a biochemical treatment apparatus, comprising:

a cartridge mounting portion for mounting a cartridge having a plurality of chambers containing a solution for biochemically treating a specimen, a plurality of nozzle portions each connected to an associated passage communicating with an associated chamber of the chambers of the cartridge, and control means for controlling a fluid pressure in the cartridge through the nozzle portions, wherein the control means controls the fluid pressure so that the solution in the cartridge is moved only in the cartridge.

According to the present invention, there is further provided a biochemical treatment process for effecting biochemical treatment in a cartridge having a plurality of chambers containing a solution for biochemically treating a specimen, the process comprising:

a step of connecting each nozzle to an associated port of a passage communicating with an associated chamber of the cartridge, and a step of injecting fluid into the cartridge to move the liquid in the cartridge.

According to the present invention, there is also provided a biochemical reaction cartridge, comprising:

a storage chamber for accumulating a liquid, a first chamber, a first passage for connecting the storage chamber to the first chamber to move the liquid in the storage chamber to the first chamber, a second chamber, and a second passage for connecting the first chamber to the second chamber to move the liquid in the first chamber to the second chamber, wherein a bottom position of a first connecting portion for connecting the first chamber to the first passage is higher than a bottom position of a second connecting portion for connecting the first chamber to the second passage.

These and other objects, features and advantages of the present invention will become more apparent upon a consideration of the following description of the preferred embodiments of the present invention taken in conjunction with the accompanying drawings.

DESCRIPTION OF THE PREFERRED EMBODIMENTS

The present invention is described more specifically below with reference to the drawings.

Embodiment 1

Figure 1:
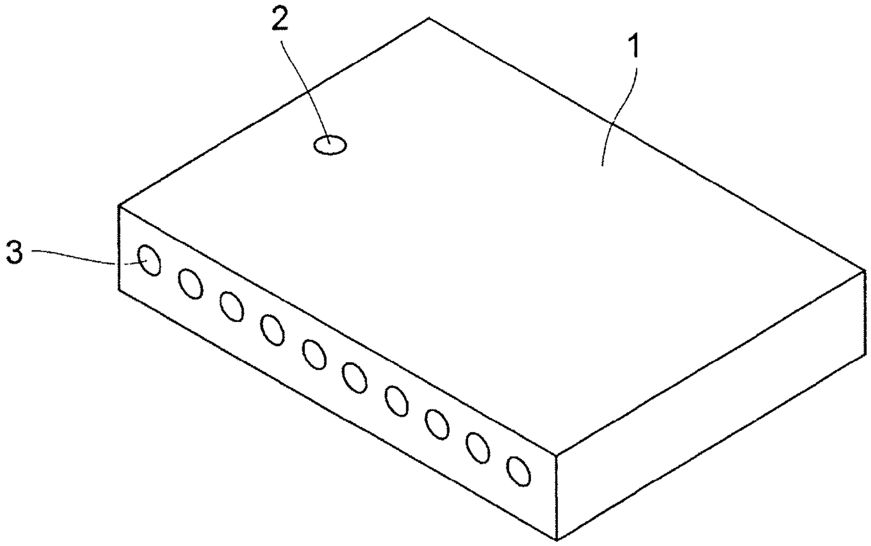
FIG. 1 is a perspective view of an embodiment of the biochemical reaction cartridge according to the present invention.

FIG. 1 is an external view of a biochemical reaction cartridge 1 in this embodiment. Referring to FIG. 1, on the cartridge 1, a specimen port 2 for injecting a specimen, such as blood, by a syringe (injector) or the like, is disposed and sealed with a rubber cap. On a side surface of the cartridge 1, there is a plurality of nozzle ports 3 into which nozzles are injected to apply or reduce pressure in order to move a solution in the cartridge 1. A rubber cap is fixed on each of the nozzle ports 3. The other side surface of the cartridge 1 has a similar structure.

A body of the biochemical reaction cartridge 1 comprises a transparent or semitransparent synthetic resin, such as polymethyl methacrylate (PMMA), acrylonitrile-butadiene-styrene (ABS) copolymer, polystyrene, polycarbonate, polyester or polyvinyl chloride. In the case where an optical measurement is not required, the material for the body of the cartridge 1 is not required to be transparent.

Figure 2:
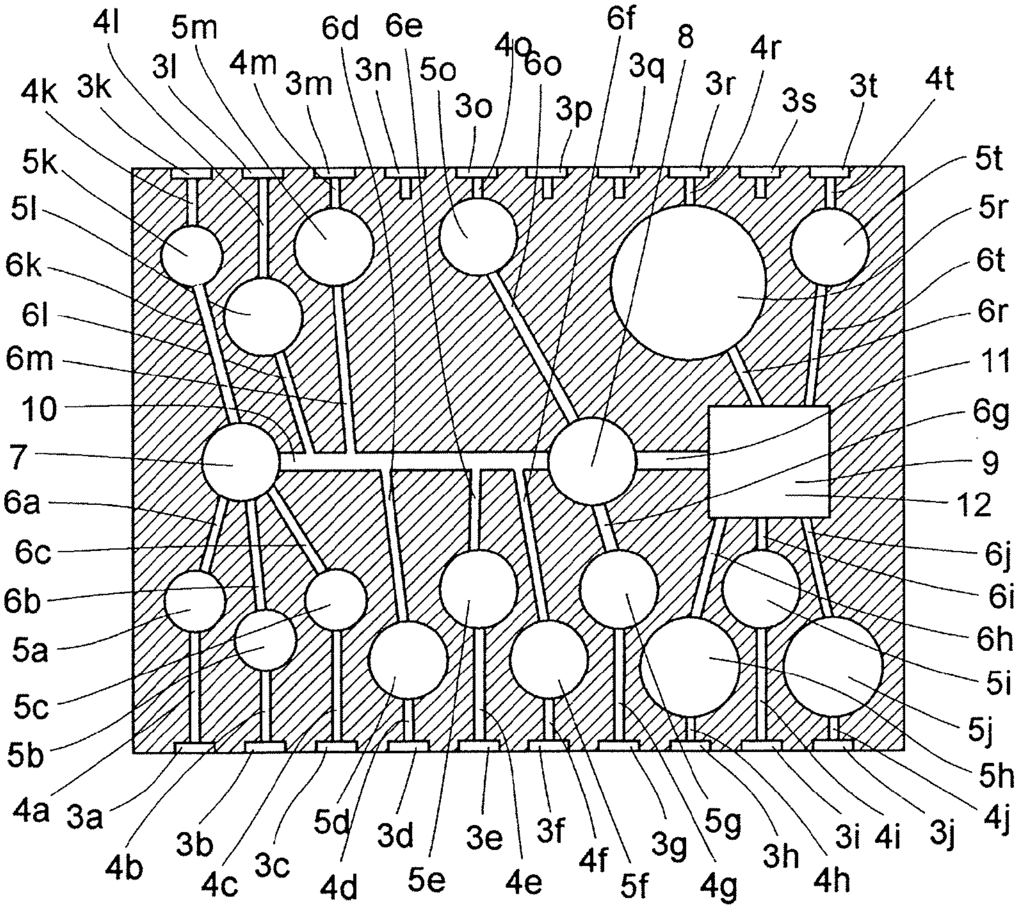
FIG. 2 is a plan view of the biochemical reaction cartridge.

FIG. 2 is a plan view of the biochemical reaction cartridge 1. Referring to FIG. 2, on one side surface of the cartridge 1, 10 nozzle ports 3*a* to 3*j* are provided. 10 nozzle ports 3*k* to 3*t* are also provided on the other side surface the cartridge 1. The respective nozzle ports 3*a* to 3*t* communicate with chambers 5, which are portions or sites for storing the solution or causing a reaction, through corresponding air passages 4*a* to 4*t*, respectively.

In this embodiment, however, the nozzle ports 3*n*, 3*p*, 3*q* and 3*s* are not used. These nozzle ports do not communicate with the chambers 5 and are used as reserve ports. More specifically, in this embodiment, the nozzle ports 3*a* to 3*j* communicate with the chambers 5*a* to 5*j* through the passages 4*a* to 4*j*, respectively. On the other side surface, the nozzle ports 3*k*, 3*l*, 3*m*, 3*o*, 3*r* and 3*t* communicate with the chambers 5*k*, 5*l*, 5*m*, 5*o*, 5*r* and 5*t* through the passages 4*k*, 4*l*, 4*m*, 4*o*, 4*r* and 4*t*, respectively.

The specimen port 2 communicates with a chamber 7. The chambers 5*a*, 5*b*, 5*c* and 5*k* communicate with the chamber 7, the chambers 5*g* and 5*o* communicate with a chamber 8, and the chambers 5*h*, 5*i*, 5*j*, 5*r* and 5*t* communicate with a chamber 9. Further, the chamber 7 communicates with the chamber 8 via a passage 10, and the chamber 8 communicates with the chamber 9 via a passage 11. The chambers 5*d*, 5*e*, 5*f*, 5*l* and 5*m* communicate with the passage 10 via passages 6*d*, 6*e*, 6*f*, 6*l*, and 6*m*, respectively. A square hole is provided at the bottom (undersurface) of the chamber 9. To the square hole, a DNA microarray 12, on which several tens to several hundred thousand different species of DNA probes are arranged at high density on a surface of a solid phase, such as a glass plate having a size of ca. square centimeter, with the probe surfaces up, is attached.

It is possible to test a large number of genes at the same time by effecting a hybridization reaction with the use of the microarray 12.

The DNA probes are regularly arranged in a matrix form, and an address (position determined by the number of rows and the number of columns in the matrix) of each of the DNA probes is readily read as information. The genes to be tested include, e.g., a genetic polymorphism of each individual, in addition to infections viruses, bacteria and disease-associated genes.

In the chambers 5*a* and 5*b*, a first hemolytic agent containing EDTA (ethylenediaminetetraacetic acid) for destructing the cell membrane and a second hemolytic agent containing a protein-modifying agent, such as a surfactant, are stored, respectively.

In the chamber 5*c*, there are stored magnetic material particles coated with silica to absorb DNA. In the chambers 5*l* and 5*m*, a first extraction cleaning liquid and a second extraction cleaning liquid, which are used for purifying DNA at the time of DNA extraction, are stored, respectively.

An eluent, comprising a buffer of a low-concentration salt, for eluting DNA from the magnetic particles, is stored in the chamber 5*d*, and a mixture liquid for PCR (polymerase chain reaction) comprising a primer, polymerase, a dNTP (deoxyribonucleotide triphosphate), a buffer, Cy-3dUTP containing a fluorescent agent, etc., is stored in the chamber 5*g*.

A cleaning agent containing a surfactant for cleaning a fluorescence-labeled specimen DNA, which is not subjected to hybridization, and a fluorescence label is stored in the chambers 5*h* and 5*j*. The alcohol for drying the inside of the chamber 9 including the DNA microarray 12 is stored in the chamber 5*i*.

The chamber 5*e* is a chamber in which debris other than DNA from blood accumulates. The chamber 5*f* is a chamber in which the waste from the first and second extraction cleaning liquids in the chambers 5*l* and 5*m* accumulates. The chamber 5*r* is a chamber in which the waste liquid from the first and second cleaning liquids accumulates. The chambers 5*k*, 5*o* and 5*t* are empty chambers provided for preventing the solution from flowing into the nozzle ports.

When the liquid specimen, such a blood, is injected into the biochemical reaction cartridge described above, and the biochemical reaction cartridge 1 is set in a treatment apparatus described below, extraction and amplification of DNA or the like are performed within the cartridge 1. Further, hybridization between the amplified specimen DNA and DNA probes on the DNA microarray disposed in the cartridge and cleaning of the fluorescence-labeled specimen DNA, which is not hybridized, and the fluorescence labeling are performed.

Figure 3:
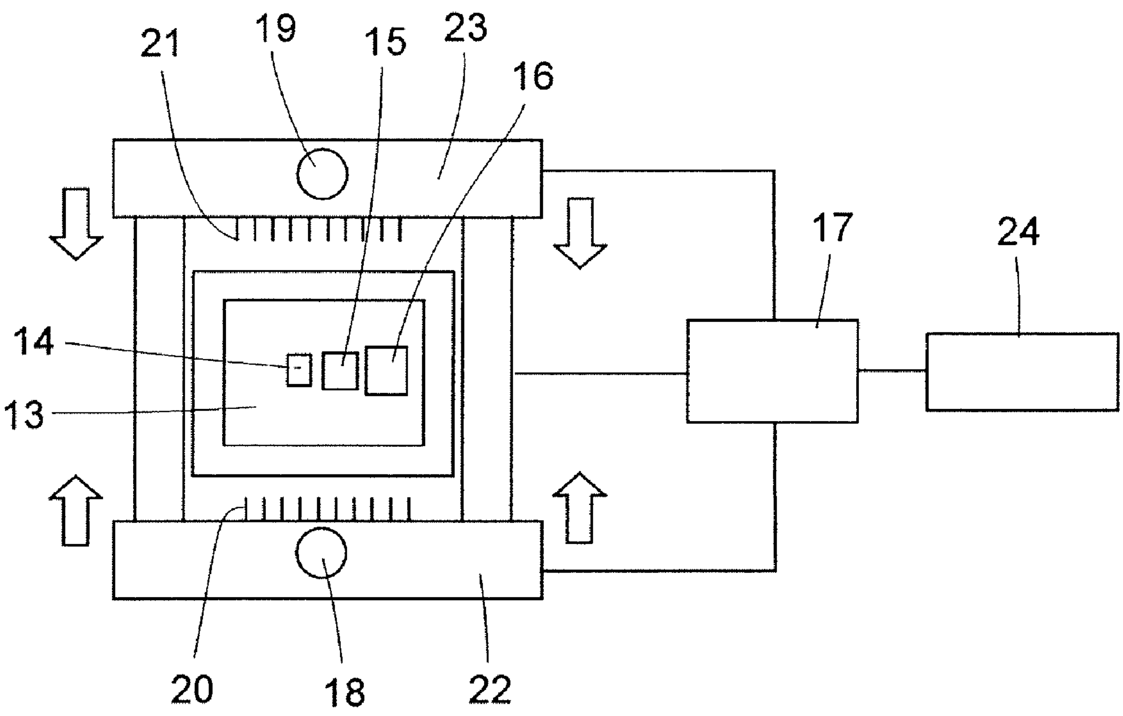
FIG. 3 is a block diagram of a treatment apparatus for controlling movement of liquid and various reactions within the biochemical reaction cartridge.

FIG. 3 is a schematic view of the treatment apparatus for controlling the movement of the solution within the biochemical reaction cartridge and various reactions.

The biochemical reaction cartridge 1 is mounted on a table 13. Further, an electromagnet 14 to be actuated at the time of extracting DNA or the like from the specimen in the cartridge 1, a Peltier element 15 for effecting temperature control at the time of amplifying DNA from the specimen through a method such as PCR (polymerase chain reaction), and a Peltier element 16 for effecting temperature control at the time of performing hybridization between the amplified specimen DNA and the DNA probe on the DNA microarray within the cartridge 1 and at the time of cleaning or washing the specimen DNA, which is not hybridized, are disposed on the table 13 and connected to a control unit 17 for controlling the entire treatment apparatus.

Electric (motor-driven) syringe pumps 18 and 19 and pump blocks 22 and 23, each of which is a port for discharging or sucking in air by these pumps 18 and 19 and is provided with 10 pump nozzles 20 or 21 on its side surface, are disposed at both side surfaces of the table 13. A plurality of electric switching (selector) valves (not shown) are disposed between the electric syringe pumps 18 and 19 and the pump nozzles 20 and 21 and connected to the control unit 17 together with the pumps 18 and 19. The control unit 17 is connected to an input unit 24, which used for inputting by a tester. The control unit 17 controls the pump nozzles 20 and 21 so that each of the respective 10 pump nozzles is selectively opened and closed with respect to the electric syringe pumps 18 and 19, respectively.

In this embodiment, when the tester injects blood as a specimen into the cartridge 1 through the rubber cap of the specimen port 2 by a syringe or an injector, the blood flows into the chamber 7. Thereafter, the tester places the biochemical reaction cartridge 1 on the table 13 and moves the pump blocks 22 and 23 in directions of arrows indicated in FIG. 3 by operating a lever (not shown), whereby the pump nozzles 20 and 21 are injected into the cartridge 1 through the corresponding nozzle ports 3 at the both side surfaces of the cartridge 1.

Further, the nozzle ports 3*a* to 3*t* are concentrated at two surfaces, i.e., both side surfaces, of the biochemical reaction cartridge 1, so that it is possible to simplify shapes and arrangements of the electric syringe pumps 18 and 19, the electric switching valves, the pump blocks 22 and 23 containing the pump nozzles, etc. Further, by effecting such a simple operation that the cartridge 1 is sandwiched between the pump blocks 22 and 23 while at the same time ensuring formation of necessary chambers 5 and passages, it is possible to inject the pump nozzles 20 and 21 and simplify the structure of the pump blocks 22 and 23. Further, all nozzle ports 3*a* to 3*t* are disposed at an identical level, i.e., are arranged linearly, whereby all the heights of the passages 4*a* to 4*t* connected to the nozzle ports 3*a* to 3*t* are equal to each other. As a result, it is easy to prepare the passages 4*a* to 4*t*.

Further, in the treatment apparatus shown in FIG. 3, in the case where the length of the pump blocks 22 and 23 is increased n times the original length with respect to n biochemical reaction cartridges 1, when the n cartridges 1 are arranged in series, it is possible to perform a necessary step for all the n cartridges 1 at the same time. As a result, a biochemical reaction can be performed in the large number of biochemical reaction cartridges with a very simple apparatus structure.

Figure 4:
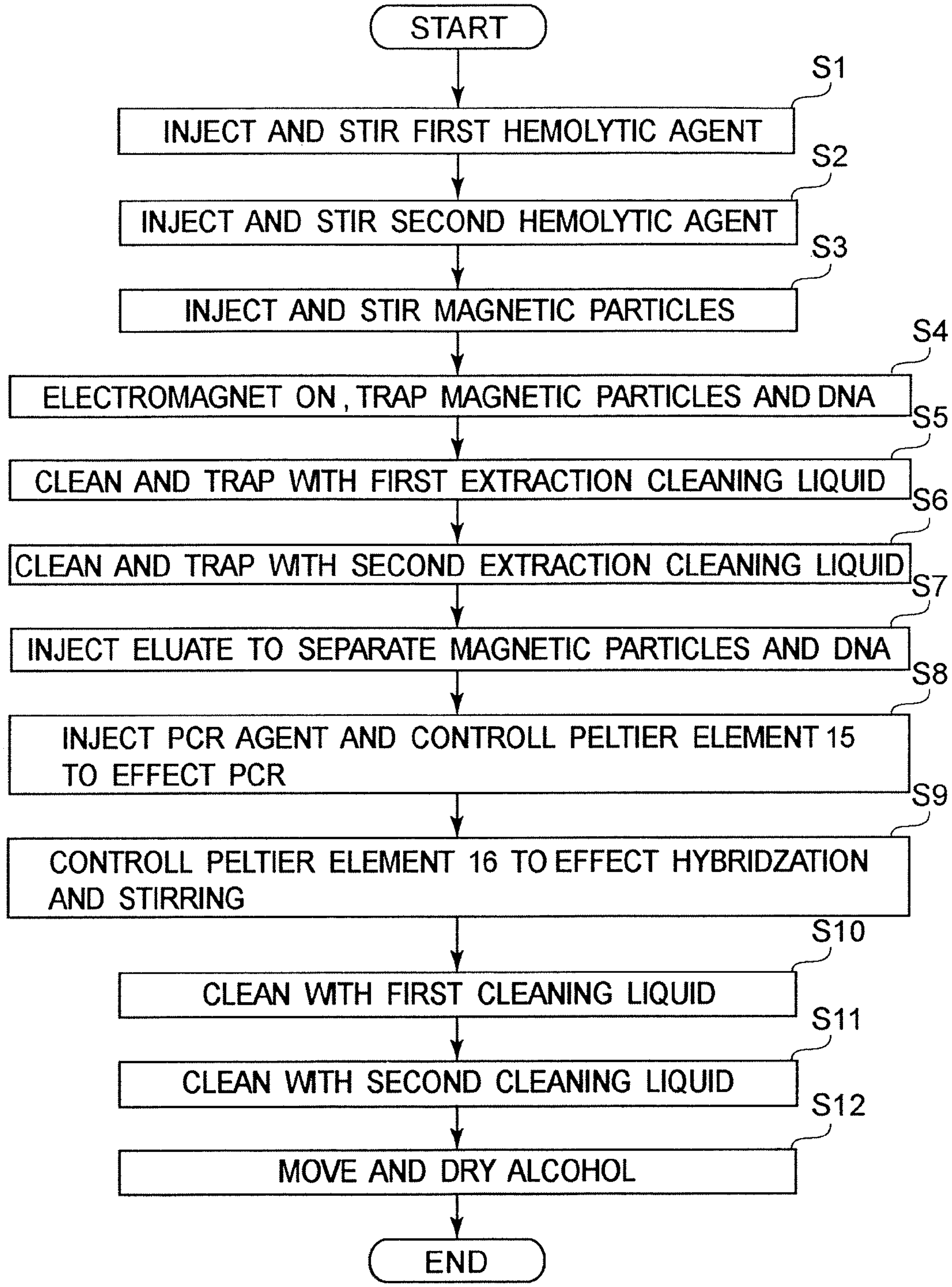
FIG. 4 is a flow chart of a treatment procedure.

Treatment starts when the tester inputs a command at the input unit 24. FIG. 4 is a flow chart for explaining a treatment procedure in the treatment apparatus in this embodiment.

Referring to FIG. 4, in step S1, the control unit 24 opens only the nozzle ports 3*a* and 3*k*, and air is discharged form the electric syringe pump 18 and sucked in the cartridge 1 from the electric syringe pump 19, whereby the first hemolytic agent is injected from the chamber 5*a* into the chamber 7 containing blood. At this time, by controlling suction of air from the pump 19 so as to start 10-200 msec after initiation of the air discharge from the pump 18, the solution can flow smoothly without splashing or being scattered at its leading end, although this depends on a viscosity of the hemolytic agent and a resistance of the passage.

As described above, by shifting the timing of the supply and suction of air so as to control the manner in which pressure is applied and reduced, it is possible to cause the solution to flow smoothly. In a preferred embodiment, the solution can be flown even more smoothly by effecting such a control that a level of air suction is linearly increased by initiating an air discharge from the pump 18. This is true in the case of subsequent liquid movement.

The air supply control can be readily realized by using the electric syringe pumps 18 and 19. More specifically, after only the nozzle ports 3*a* and 3*o* are opened, discharge and suction of air are repeated alternately by the pumps 18 and 19 to cause a repetitive flow and flow-back of the solution from the chamber 7 in the passage 10, thus stirring the solution. Alternatively, the solution can be stirred while continuously discharging air from the pump 19 to generate bubbles.

Figure 5:
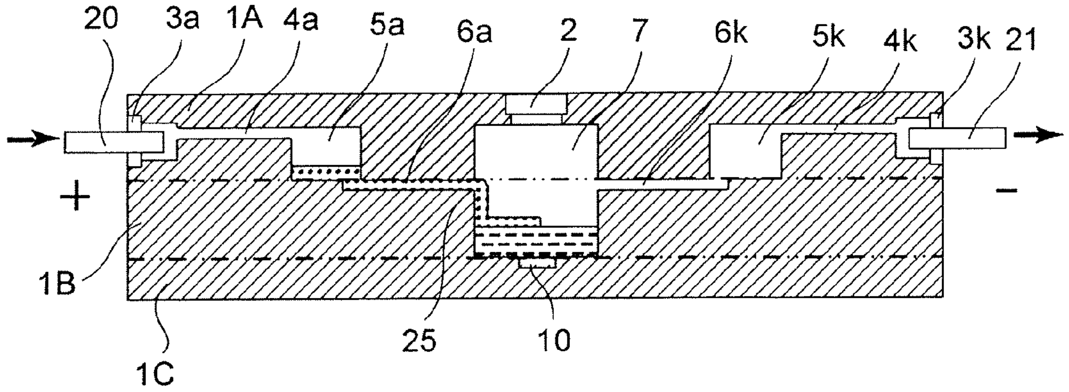
FIG. 5 is a longitudinal sectional view of a part of a chamber.

FIG. 5 is a sectional view of the biochemical reaction cartridge 1 shown in FIG. 2 along a cross-section intersecting the chambers 5*a*, 7 and 5*k*, and shows a state in which the nozzle port 3*a* is pressurized by injecting therein the pump nozzle 20, and the nozzle port 3*k* is reduced in pressure by injecting therein the pump nozzle 21, whereby the first hemolytic agent in the chamber 5*a* flows into the chamber 7 through the passage 6*a*. In FIG. 5, in order to clarify a height (level) relationship, a cross-section of the passage 10 is also shown.

A volume of the first hemolytic agent in the chamber 5*a* is determined, so that it meets the requirement. Further, dimensions and positions of the chambers 5*a* and 7 are determined, so that the liquid level in the chamber 7 is lower than a height (vertical position) of a bottom surface 25 of a connecting portion between the passage 6*a* and the chamber 7 when the first hemolytic agent flows into the chamber 7.

Referring again to FIG. 4, in step S2, only the nozzle ports 3*b* and 3*k* are opened, and the second hemolytic agent in the chamber 5*b* is caused to flow into the chamber 7 in the same manner as in the case of the first hemolytic agent. Similarly, in step S3, the magnetic particles in the chamber 5*c* are caused to flow into the chamber 7. In steps S2 and S3, stirring is performed in the same manner as in step S1. In step S3, DNA resulting from dissolution of cells in steps S1 and S2 attaches to the magnetic particles.

Cross-sectional shapes of the chambers 5*b* and 5*c* and the passages 6*b* and 6*c* are the same as those of the chamber 5*a* and the passage 6*a*. Volumes of the second hemolytic agent and the magnetic particle solution are determined, so that they meet their requirements. Further, as in step S1, dimensions and positions of the chambers 5*b*, 5*c* and 7 are determined, so that the liquid level in the chamber 7 is lower than the height of the bottom surfaces of connecting portions between the passages 6*b* and 6*c* and the chamber 7.

Incidentally, in this embodiment, the biochemical reaction cartridge 1 is prepared through ultrasonic fusion bonding of three injection molded parts 1A, 1B and 1C marked by chain double-dashed lines in FIG. 5. For convenience during the manufacturing process, the passages 6*a*, 6*b* and 6*c* are identical in height (vertical position). Accordingly, the associated connection portions are also at the same height. Further, the chambers having the same height as the chambers 5*a*, 5*b* and 5*c* are the chamber 5*k* shown in FIG. 1 and the chambers 5*g* and 5*o* shown in FIG. 2.

Due to this arrangement, the reagent flows from a higher position than the chamber to which it is to be moved, so that it is possible to smoothly and reliably move the entire amount of the reagent stored in the storage chamber with less resistance. Further, in some cases, for some reagents, it is desirable to avoid generation of bubbles. In such cases, when the movement of the reagent is performed as described above, the entire amount of the solution can be moved using a simple structure while avoiding the generation of bubbles without monitoring the movement of the solution to completion.

Thereafter, in step S4, an electromagnet 14 is turned on and only the nozzle ports 3*e* and 3*k* are opened. Then, air is discharged from the electric syringe pump 19 and sucked in form the pump 18 to move the solution from the chamber 7 to the chamber 5*e*. At the time of movement, the magnetic particles and DNA are trapped in the passage 10 on the electromagnet 14. The suction and discharge by the pumps 18 and 19 are alternately repeated to reciprocate the solution two times between the chambers 7 and 5*e*, whereby the efficiency of trapping DNA is improved. The trapping efficiency can be further improved by increasing the number of reciprocations. In this case, however, the treatment time increases accordingly.

As described above, DNA is trapped in a flowing state in a small passage having a width of about 1-2 mm and a height of about 0.2-1 mm by utilizing the magnetic particles, so that DNA can be trapped at a high efficiency. This is also true for RNA and proteins.

Figure 6:
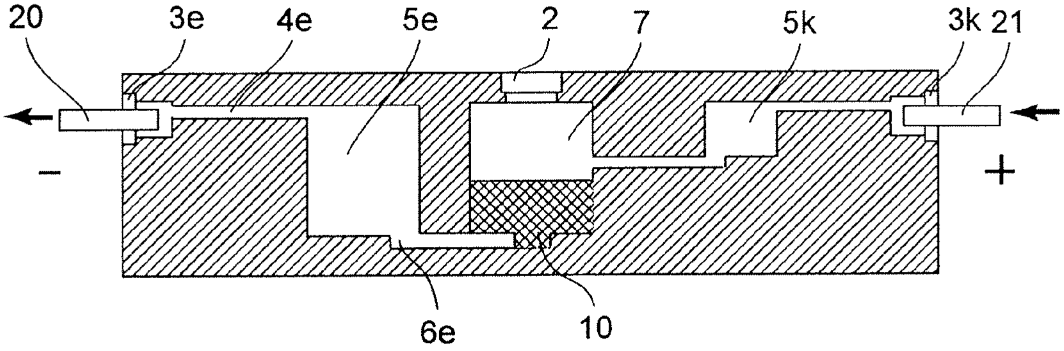
FIG. 6 is a longitudinal sectional view of another part of the chamber.

FIG. 6 is a sectional view of the cartridge 1 shown in FIG. 2 along a cross-section intersecting the chambers 5*e*, 7 and 5*k*. FIG. 6 shows a height relationship between the chambers 5*e* and 7 and the passage 6*e*. The passage 6*e* connects the bottom portions of the chambers 5*e* and 7, so that the movement direction of the solution is reversed when the suction by the pump 18 and the discharge by the pump 19 are reversed. As a result, when the suction and the discharge are alternately repeated, it is possible to reciprocate the solution any number of times between the chambers 7 and 5*e*.

Then, in step S5, the electromagnet 14 is turned off, and only the nozzle ports 3*f* and 3*l* are opened. Thereafter, air is discharged from the electric syringe pump 19 and sucked in from the pump 18 to move the first extraction cleaning liquid from the chamber 5*ll* to the chamber 5*f*. At this time, the magnetic particles and DNA trapped in step S4 are moved together with the extraction cleaning liquid, whereby cleaning is performed. After the reciprocation is performed two times in the same manner as in step S4, the electromagnet 14 is turned on, and the reciprocation is similarly performed two times to recover the magnetic particles and DNA in the passage 10 on the electromagnet 14 to return the solution to the chamber 5*l*.

In step S6, cleaning is further performed in the same manner as in step S5 by using the second extraction cleaning liquid in the chamber 5*m* in combination with the nozzle ports 3*f* and 3*m*.

In step S7, only the nozzle ports 3*d* and 3*o* are opened while the electromagnet 14 is kept on, and air is discharged from the pump 18 and sucked in from the pump 19, whereby the eluent in the chamber 5*d* is moved to the chamber 8.

At this time, the magnetic particles and DNA are separated by the action of the eluent, so that only the DNA is moved together with the eluent to the chamber 8, and the magnetic particles remain in the passage 10. Thus, extraction and purification of the DNA are performed. As described above, the chamber containing the extraction cleaning liquid and the chamber containing waste liquid after the cleaning are separately provided, so that it becomes possible to effect extraction and purification of the DNA in the biochemical reaction cartridge 1.

Next, in step S8, only the nozzle ports 3*g* and 3*o* are opened, and air is discharged from the electric syringe pump 18 and sucked in from the pump 19 to cause the PCR agent in the chamber 5*g* to flow into the chamber 8. Further, only the nozzle ports 3*g* and 3*t* are opened, and air discharge and suction by the pumps 18 and 19 are repeated alternately to cause repetitive flow and flow-back of the solution of the chamber 8 in the passage 11, thus stirring the solution. Then, the Peltier element 15 is controlled to retain the solution in the chamber 8 at 96 □C for 10 min. Thereafter, a cycle of heating at 96 □C/10 sec, 55° C./10 sec, and 72° C./1 min. is repeated 30 times, thus subjecting the eluted DNA to PCR to amplify the DNA.

In step S9, only the nozzle ports 3*g* and 3*t* are opened, and air is discharged from the electric syringe pump 18 and sucked in from the pump 19 to move the solution in the chamber 8 to the chamber 9. Further, by controlling the Peltier element 16, the solution in the chamber 9 is kept at 45° C. for 2 hours to effect the hybridization. At this time, discharge and suction of air by the pumps 18 and 19 are repeated alternately to move the solution between the chamber 9 and the passage 6*t*, which stirs the solution.

In step S10, while keeping the temperature at 45° C., only the nozzle ports 3*h* and 3*r* are opened, and air is discharged from the electric syringe pump 18 and sucked in from the pump 19 to cause the first cleaning liquid in the chamber 5*h* to flow into the chamber 5*r* through the chamber 9 while moving the solution in the chamber 9 to the chamber 5*r*. The suction and discharge by the pumps 18 and 19 are repeated alternately to reciprocate the solution two times between the chambers 5*h*, 9 and 5*r* and finally return the solution to the chamber 5*h*. Thus, the fluorescence-labeled specimen DNA and the fluorescence label, which are not hybridized, are cleaned.

Figure 7:
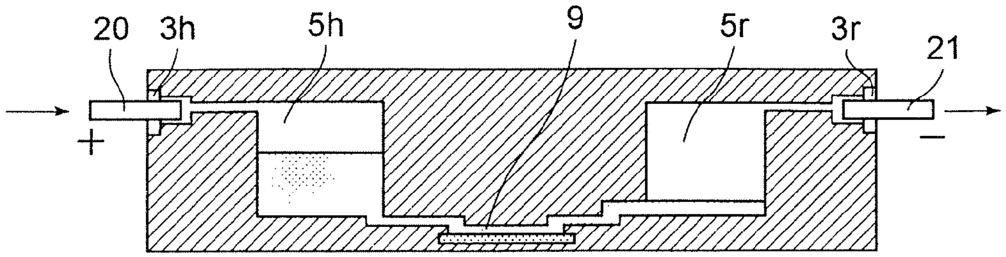
FIG. 7 is a longitudinal sectional view of another part of the chamber.

FIG. 7 is a sectional view of the biochemical reaction cartridge 1 shown in FIG. 2 along a cross-section intersecting the chambers 5*h*, 9 and 5*r*. The cartridge 1 is pressurized by injecting the pump nozzle 20 into the nozzle port 3*h* and is reduced in pressure by injecting the pump nozzle 21 into the nozzle port 3*r*. FIG. 7 illustrates a state in which the first cleaning liquid is caused to flow into the chamber 5*r* through the chamber 9.

Referring again to FIG. 4, in step S11, the cleaning is further effected while maintaining the temperature at 45° C. in the same manner as in step S10 by using the second cleaning liquid in the chamber 5*j* in combination with the nozzle ports 3*j* and 3*r*, and the solution is finally returned to the chamber 5*j*. As described above, the chambers 5*h* and 5*j* containing the cleaning liquids and the chamber 5*r* containing the waste liquid after the cleaning are separately provided, so that it becomes possible to clean the DNA microarray 12 in the biochemical reaction cartridge 1.

In step 12, only the nozzle ports 3*i* and 3*r* are opened, and air is discharged from the electric syringe pump 18 and sucked in from the pump 19 to move the alcohol in the chamber 5*i* to the chamber 5*r* through the chamber 9. Thereafter, only the nozzle port 3*i* and 3*t* are opened, and air is discharged from the pump 18 and sucked in from the pump 19 to dry the chamber 9.

When the tester operates a lever (not shown), the pump blocks 22 and 23 are moved away from the biochemical reaction cartridge 1. As a result, the pump nozzles 20 and 21 are removed from the nozzle ports 3 of the cartridge 1. Then, the tester mounts the cartridge 1 in a reader for the DNA array, such as a known scanner, to effect the measurement and analysis.

Embodiment 2

Figure 8:
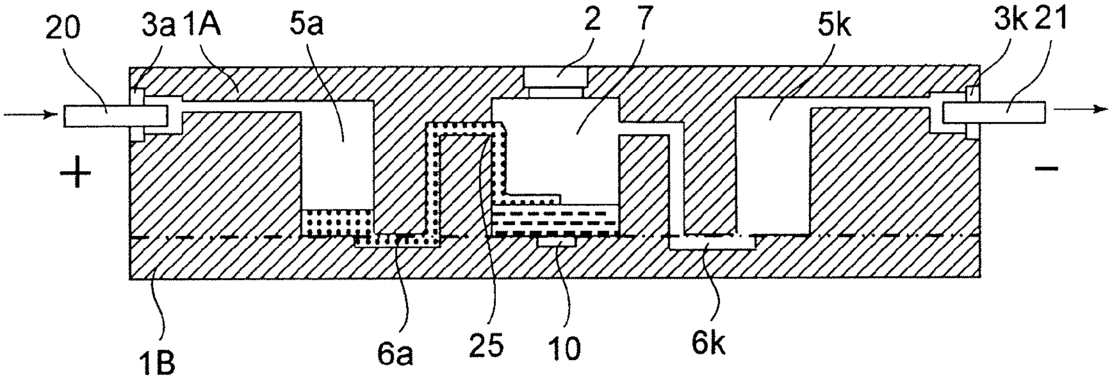
FIG. 8 is a longitudinal sectional view of a part of a chamber according to another embodiment.

FIG. 8 is a sectional view of a biochemical reaction cartridge 1 of this embodiment, and illustrates a cross-section intersecting the chambers 5*a*, 7 and 5*k* shown in FIG. 2 of Embodiment 1. Further, FIGS. 1 to 4 and 7 in Embodiment 1 are also applicable to this embodiment.

The biochemical reaction cartridge 1 is pressurized by injecting the pump nozzle 20 into the nozzle port 3*a*, and the pressure is reduced by injecting the pump nozzle 21 into the nozzle port 3*k*. FIG. 8 illustrates a state in which a first hemolytic agent in the chamber 5*a* is caused to flow into the chamber 7 containing blood through the passage 6*a*. In order to clarify a height relationship, a cross-section of the passage is also indicated.

In this embodiment, the passage connecting the chambers 5*a* and 7 extends not only in a horizontal direction, but also in a vertical direction, so that a (vertical) height of a bottom surface 25 of the connection portion between the passage 6*a* and the chamber 7 is increased, i.e., a permissible liquid level is increased. As a result, the amount of a solution that can be contained in the chamber 7 is increased. If it is not necessary to increase the solution amount, the height of the biochemical reaction cartridge 1 can be decreased.

Further, in the case of preparing the biochemical reaction cartridge 1 by injection molding, the vertical portion of the passage 6*a* is required in this embodiment. However, it can be provided by using two injection-molded parts A and B marked by a chain double-dashed line in FIG. 8. Alternatively, it is also possible to bond two sheet parts to each other. In this case, the passage 6*a* may be tilted to have an oblique surface.

In the above embodiments (Embodiments 1 and 2), the movement from the storage chamber is performed with respect to the reagent, but may also be performed with respect to the liquid specimen or cleaning liquid. Further, in the above embodiments, the movement of the liquid is performed by applying pressure and reducing the amount of air, but may also be performed in a different manner, such that the cartridge 1 is opened at one side surface and only pressurized, or the pressure is reduced, at the other side surface. Also, a pump, which directly moves a solution, may be used, or the movement by utilizing an electrical or a magnetic force may be adopted. Further, in the above embodiments, a predetermined amount of the solution is stored in the storage chamber, and all of the solution is moved. However, the amount of the moving solution may also be controlled by a liquid amount sensor or a flow rate sensor.

As described above, according to the present invention, the solution moves only inside the biochemical reaction cartridge by an external pump without having to incorporate the pump into the structure of the cartridge in order to cause the necessary reaction to proceed. Thus, it is possible to provide a disposable, inexpensive cartridge from which the solution does not escape. As a result, the possibilities of a secondary infection and contamination are eliminated. Further, the cartridge incorporates therein the necessary solution, so that there is no need to prepare a reagent and cleaning liquids. As a result, it is possible to eliminate manual process steps and prevent reagent selection errors from occurring.

Further, according to the present invention, air pressure within the cartridge is controlled by the (external) pump on the treatment apparatus side to move the solution only within the cartridge, thus causing a necessary biochemical reaction to proceed. Accordingly, it is possible to effect the biochemical reaction within the cartridge by using an inexpensive biochemical reaction cartridge.

Also, the biochemical reaction cartridge according to the present invention can reliably effect movement, including the return, of both the reagent and the specimen within its simple structure by properly using an optimum passage for each of these materials. Further, the structure of the cartridge in accordance with the present invention makes it possible to move a liquid, such as a reagent or a liquid specimen, efficiently to a subsequent chamber without generating bubbles.

While the invention has been described with reference to the structures disclosed herein, it is not limited to the details set forth, and this application is intended to cover such modifications or changes as may come within the purposes of the improvements or the scope of the following claims.

I claim:

1. A biochemical reaction cartridge, comprising:

a storage chamber for accumulating a liquid containing a reagent, a first function chamber, having a specimen port, for mixing a predetermined amount of the liquid with a predetermined amount of a specimen, a second function chamber, for reciprocating the liquid mixed with the specimen in the first function chamber, a first passage for connecting a bottom of the storage chamber to the first function chamber to move the liquid from the storage chamber to the first function chamber, a second passage for connecting a bottom of the first function chamber to a bottom of the second function chamber to reciprocally move the liquid between the first function chamber and the second function chamber, a first connecting portion, for connecting the first function chamber to the first passage, having a bottom position, and a second connecting portion, for connecting the first function chamber to the second passage, having a bottom position, wherein the first passage has a connecting portion, for connecting the first passage to the first function chamber, having a height greater than a liquid surface of the liquid mixed with the specimen in the first function chamber.

2. The cartridge according to claim 1, wherein the cartridge comprises a pressure reducing portion for externally reducing the pressure, the pressure reducing portion being provided with a chamber for preventing outflow of the liquid.

3. The cartridge according to claim 1, wherein the cartridge further comprises a plurality of nozzle ports for receiving a plurality of nozzles for applying or reducing pressure, the plurality of nozzle ports communicating with the first or second function chamber, and wherein fluid is present between the plurality of nozzle ports and the first or second function chamber and is pressurized or depressurized by the plurality of nozzles to move the specimen and/or the reagent and/or the reaction liquid, thereby to effect a sequence of a biochemical reaction within the cartridge.

4. The cartridge according to claim 3, wherein the plurality of nozzle ports are divided into two portions, which are disposed on two surfaces of the cartridge, and the cartridge is a substantially rectangular parallelepiped, and the two surfaces are opposite lateral surfaces of the substantially rectangular parallelepiped.

5. The cartridge according to claim 1, wherein a bottom position of a connecting portion for connecting the first passage to the first function chamber is different from a bottom position of the storage chamber and a bottom position of the first connecting passage, and a bottom position of another connecting portion for connecting the second passage to the first function chamber is different from a bottom position of the first function chamber and a bottom position of the second passage.

6. The cartridge according to claim 1, wherein the chambers and the passages are formed with a plurality of members, which have been laminated.

7. A biochemical reaction cartridge, comprising:

a storage chamber for accumulating a liquid containing a reagent, a first function chamber, having a specimen port, for mixing a predetermined amount of the liquid with a predetermined amount of a specimen, a second function chamber, for reciprocating the liquid mixed with the specimen in the first function chamber, a first passage for connecting a bottom of the storage chamber to the first function chamber to move the liquid from the storage chamber to the first function chamber, and a second passage for connecting a bottom of the first function chamber to a bottom of the second function chamber to reciprocally move the liquid between the first function chamber and the second function chamber, wherein the first passage has a first connecting portion, for connecting the first passage to the first function chamber, having a height greater than a liquid surface of the liquid mixed with the specimen in the first function chamber, and wherein the second passage has a second connecting portion, for connecting the second passage to the first function chamber, having a height smaller than the liquid surface of the liquid mixed with the specimen in the first function chamber.

* * * * *